US00PP27154P2

(12) United States Plant Patent
Deng et al.

(10) Patent No.: US PP27,154 P2
(45) Date of Patent: Sep. 13, 2016

(54) ***CALADIUM* PLANT NAMED 'COSMIC DELIGHT'**

(50) Latin Name: *Caladium×hortulanum*
Varietal Denomination: Cosmic Delight

(71) Applicant: Florida Foundation Seed Producers, Inc., Marianna, FL (US)

(72) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/998,920

(22) Filed: Mar. 4, 2016

(51) Int. Cl.
*A01H 5/12* (2006.01)

(52) U.S. Cl.
USPC ..... Plt./373

(58) Field of Classification Search
USPC ..... Plt./263.1, 373
See application file for complete search history.

(56) References Cited

U.S. PATENT DOCUMENTS

PP14,402 P2 12/2003 Miranda
PP14,565 P2 2/2004 Harbaugh et al.

*Primary Examiner* — Susan McCormick Ewoldt
*Assistant Examiner* — Karen Redden
(74) *Attorney, Agent, or Firm* — Christopher & Weisberg, P.A.

(57) ABSTRACT

A new and distinct cultivar of *Caladium* plant named 'Cosmic Delight', characterized by its outwardly arching growth habit, wide lance leaves that have a creamy-white center, creamy-white veins, light pink to red spots, green mottling, and green margins, tolerance to sunburns, high tuber yield potential, and good performance in sunny or shady landscapes.

2 Drawing Sheets

ACKNOWLEDGMENT OF FEDERAL RESEARCH SUPPORT

This invention was made with government support under FLA-BRA-04162 awarded by the Cooperative State Research, Education, and Extension Service, USDA and under FLA-GCR-005065 awarded by the National Institute of Food and Agriculture, USDA. The government has certain rights in the invention.

Genus and species: *Caladium×hortulanum.*

Cultivar denomination: 'Cosmic Delight'.

CROSS-REFERENCE TO RELATED APPLICATION n/a

BACKGROUND OF THE NEW CULTIVAR

The present invention relates to a new and distinct cultivar of *caladium* plant, botanically known as *Caladium×hortulanum*, commercially referred to as a strap leaf-type or lance leaf-type *caladium* and hereinafter referred to by the name 'Cosmic Delight'.

*Caladiums* (also referred to as *Caladium* plants) are ornamental aroids frequently used as pot and landscape plants for their colorful foliage and ease of growing. The objective of the Inventors' breeding program is to create new *Caladium* cultivars that have compact growth habit, numerous leaves, attractive foliage, and exceptional container and landscape performance.

The new *Caladium* cultivar 'Cosmic Delight' originated from a cross between 'Gingerland' (commercial cultivar, not patented) and 'Florida Moonlight', a patented cultivar (U.S. Plant Pat. No. 14,565) that was made in Bradenton, Fla., in 2001. The new *Caladium* cultivar 'Cosmic Delight' was discovered and selected by the inventors as a single plant in Bradenton, Fla. in 2002. The *Caladium* cultivar 'Cosmic Delight' has been found to retain its distinctive characteristics through at least ten generations of successive asexual propagations via tuber divisions since 2002.

Plant Breeder's Rights for this cultivar have not been applied for. 'Cosmic Delight' has not been made publicly available more than one year prior to the filing of this application.

SUMMARY OF THE INVENTION

The new *Caladium* cultivar has not been observed under all possible environmental conditions. The phenotype may vary somewhat with variations in environment such as temperature, light intensity, water status, fertilizer rate and type, without, however, any variance in genotype.

The following are the most outstanding and distinguishing characteristics of this new *Caladium* cultivar when grown under (normal or standard) horticultural practices in Wimauma, Fla. The combination of these characteristics distinguishes 'Cosmic Delight' as a new and distinct cultivar of *Caladium:*

1. Outwardly arching plant form;
2. Mounding, bushy growth habit;
3. Wide lance leaves have distinctive dark green margins with a white center accented with light pink to red spots, and green to greyed green mottling. The mid rib is white and the primary veins are yellow-green;

4. Good tolerance to sunburn or shading; and
5. Attractive plants in containers or sunny or shady landscapes.

'The new cultivar 'Cosmic Delight' differs from its female parent 'Gingerland' in the following characteristics:

1. Leaves of the new cultivar have fewer spots than the leaves of 'Gingerland'.
2. The spots on leaves of the new cultivar have lighter colors than the spots of 'Gingerland'.
3. Petioles of mature leaves of the new cultivar arch more upward and have a distinctive coloring of greyed red at the proximal end and yellow-green at the distal end, whereas the petioles of 'Gingerland' are uniformly green to pinkish in color from the proximal to the distal end.

The new *Caladium* cultivar 'Cosmic Delight' differs from its male parent 'Florida Moonlight' in the following characteristics:

1. Leaves of the new cultivar are of the lance type with wider green margins, versus the fancy heart-shaped leaves of 'Florida Moonlight' that have very narrow green margins.
2. Leaves of the new cultivar 'Cosmic Delight' have light pink to red spots and green patches, whereas leaves of 'Florida Moonlight' have no spots or blotching.

DESCRIPTION OF THE FIGURES

The accompanying photographs (as shown in FIGS. 1-2) illustrate the overall appearance of the new *Caladium* cultivar.

These photographs show the colors as true as can be reasonably obtained in colored reproductions of this type. Colors in the photographs may differ slightly from the color values cited in the detailed botanical description, which accurately describe the colors of the new *Caladium* cultivar.

DETAILED BOTANICAL DESCRIPTION OF THE CULTIVAR

Figure 1:
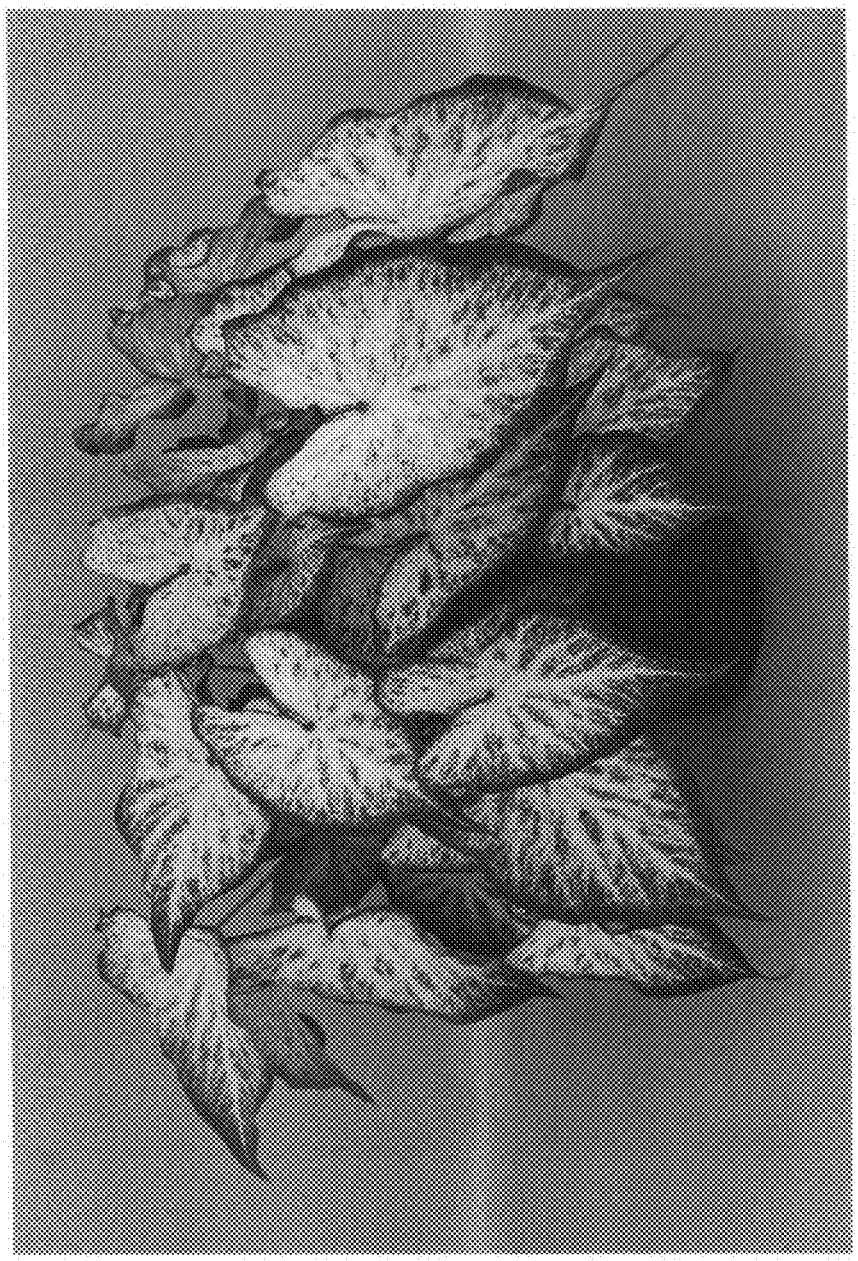
FIG. 1 shows a photograph of a side view of a typical plant of the new *Caladium* cultivar 'Cosmic Delight' grown in a 20.3-cm diameter container in a shadehouse.
Figure 2:
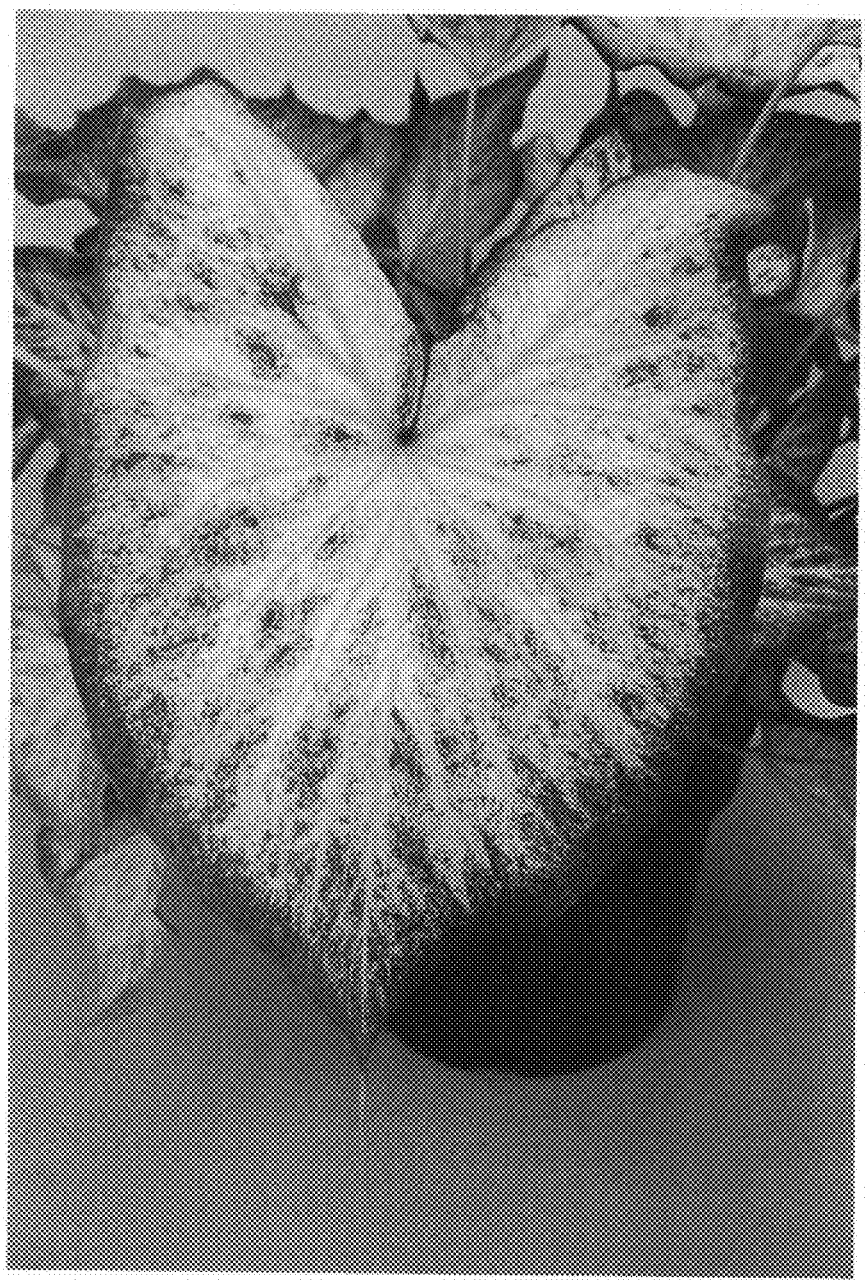
FIG. 2 shows a photograph of a top view of a typical leaf of the new *Caladium* cultivar 'Cosmic Delight' grown in a 20.3-cm diameter container in a shadehouse.

In the following description, color references are made to The Royal Horticultural Society (R.H.S.) Colour Chart, 1986 Edition, except where general terms of ordinary dictionary significance are used. The features of 'Cosmic Delight' described herein are shown in FIGS. 1-2.

Description of Growing Conditions

The following observations and measurements describe plants grown in 20.3-cm containers in Wimauma, Fla., during the summer of 2015 in a polypropylene-covered shadehouse. All plants were grown under conditions and practices similar to those generally used in commercial *Caladium* production.

During the production of the plants, day temperatures ranged from approximately 75° F. to 92° F., night temperatures ranged from approximately 66.5° F. to 76.1° F., and the shadehouse was covered with shadecloth that excluded approximately 30% natural light. Plants grown in the shadehouse were approximately seven weeks from planting tubers when the photographs and the detailed description were taken.

Botanical Description

Botanical classification:
- *Family*.—Araceae.
- *Botanical name*.—*Caladium×hortulanum*.
- *Common name*.—*Caladium*.
- *Cultivar*.—'Cosmic Delight' (*Caladium×hortulanum* cultivar 'Cosmic Delight').

Parentage:
- *Female or seed parent*.—'Gingerland'.
- *Male or pollen parent*.—'Florida Moonlight' (U.S. Plant Pat. No. 14,565).

Propagation:
- *Type*.—By tubers and by tuber divisions.
- *Time to initiate roots, summer*.—Approximately seven to ten days at 32° C.
- *Time to initiate roots, winter*.—Approximately two to three weeks at 24° C.

Tuber description: Jumbo-sized (6.4 to 8.9 cm in diameter) tubers are multi-segmented, bearing six to nine dominant buds.
- *Height of tubers*.—3.3 to 3.9 cm.
- *Diameter of tubers*.—6.5 to 8.5 cm.
- *Texture*.—Thick, starchy inside; slightly brittle between tuber segments.
- *Color*.—Epidermis, Close to brown (RHS 200B). Interior, yellow (RHS 10C).
- *Root description*.—Dense, thick and white fleshy roots white (RHS 155D).

Plant description:
- *Type*.—Herbaceous perennial.
- *Plant form*.—Outwardly arching plant.
- *Growth habit*.—Leaf petioles arising from tubers; petioles mostly semi-upright and curving outwardly with development; multiple leaves forming a relatively dense canopy; suitable for growing in containers with 10.0 cm or larger diameters.
- *Plant height, from soil level to top of leaf plane, shadehouse-grown plants*.—Approximately 39.6 cm.
- *Plant spread, shadehouse-grown plants*.—Approximately 40 cm×78 cm.

Foliage description (shadehouse-grown):
- *Length, shadehouse-grown plants*.—Approximately 25 cm.
- *Width, shadehouse-grown plants (flattened)*.—Approximately 17 cm.
- *Shape*.—Ovate.
- *Apex*.—Acuminate to acute.
- *Base*.—Cordate.
- *Margin*.—Entire.
- *Texture, upper surface*.—Smooth, glabrous.
- *Texture, lower surface*.—Smooth, glabrous; glaucous.
- *Venation pattern*.—Palmate-pinnate.

Leaf color, shadehouse-grown plants:
- *Fully expanded leaves*.—Upper surface: Center: Close to green-white (RHS 157D), with numerous patches of green (RHS 137A) and greyed-green (RHS 193C) and spots of red-purple (RHS 60A) of variable sizes. May have a thin line of red-purple (RHS 60B) along the leaf edge from the notch through the sinus cavity. Border and margins: Close to green (RHS 137A);

mottling of green (RHS 137A) along the margins. Basal notch: Close to red-purple (RHS 60B). May be variable. Venation: Midrib: Close to green-white (RHS 157C). Primary: Close to yellow-green (RHS 145C to 145D). Lower surface: Center: Close to white (RHS 155B), with large blotches of greyed-green (RHS 191A) and dashes of greyed-purple (RHS 186A) through the leaf surface. Border and margins: Close to greyed-green (RHS 191A) and specks of greyed-purple (RHS 186A). Venation: Midrib: Close to yellow-green (RHS 145B). Primary veins: Close to yellow-green (RHS144A to 144B).

Petiole:

*Aspect*.—Mostly semi-erect, curving outwardly with development.

*Length, shadehouse-grown plants*.—Approximately 25 to 34 cm.

*Diameter, distal, shadehouse-grown plants*.—Approximately 4.6 mm.

*Diameter, proximal, shadehouse-grown plants*.—Approximately 8.1 mm.

*Strength*.—Strong and flexible.

*Color, shadehouse-grown plants*.—Lower ⅔ close to greyed-red (RHS 182D) but lighter, with dashes of brown (RHS 200B). Upper ⅓ close to green (RHS 143B).

*Wing length, shadehouse-grown plants*.—Approximately 6.5.0 cm to 9 cm.

*Wing diameter, shadehouse-grown plants*.—Approximately 5.0 mm to 9.3 mm.

*Wing color, shadehouse-grown plants*.—Close to greyed-red (RHS 182D) but lighter with dashes of brown (200B).

Inflorescence description: None observed on plants of 'Cosmic Delight' to date.

Disease/pest resistance: Plants of 'Cosmic Delight' have been observed to be resistant to *Xanthomonas* leaf spot.

Temperature tolerance: Tolerant to temperatures ranging from approximately 7° C. to approximately 40° C.

Sunburn tolerance: Moderate to high levels of tolerance to sunburns.

Comparison with Known Cultivars

The new cultivar 'Cosmic Delight' was evaluated for tuber production in Wimauma, Fla. in 2007 and 2014. The soil was EauGallie fine sand with about 1% organic matter and a pH value between 6.2 and 7.4. *Caladium* plants were grown in the field using a plastic-mulched raised-bed system. For the 2007 evaluation, ground beds (81 cm wide, 20 cm high) were fumigated on 3 April with a mixture of 67% methyl bromide and 33% chloropicrin (by volume) at the rate of 196 $kg \cdot ha^{-1}$. *Caladium* seed pieces (tuber pieces, approximately 2.5×2.5×2.5 cm) were planted manually on 26 April with approximately 25.4 cm between-row spacing and approximately 15.2 cm in-row spacing. Drip tapes were buried under the plastic mulch and delivered approximately 6 mm of water to the bed per day. Fertigation (through the drip irrigation system) began when young *caladium* plants emerged from the soil, supplying soluble fertilizer (6N-0.8P-3.9K) at the rate of approximately 1.9 kg of $nitrogen \cdot ha^{-1} \cdot day^{-1}$ and a total 290 kg of $nitrogen \cdot ha^{-1}$ per growing season. Tubers (new crop) were dug, washed, and dried in early January 2008. Dried tubers from each experimental field plot were weighed, graded, and counted in late January 2008. Tuber grading was by the tuber maximum diameter: Super Mammoth (greater than 11.4 cm), Mammoth (8.9 to 11.4 cm), Jumbo (6.4 to 8.9 cm), No.1 (3.8 to 6.4 cm), and No. 2 (2.5 to 3.8 cm). Tuber grades and counts were converted into a Production Index (PI) to show the relative economic value of the harvested tubers per field plot: PI=8n (Supper Mammoth)+6n (Mammoth)+4n (Jumbo)+2n (No.1)+1n (No.2), where n=number of tubers in the grade. The relative values assigned to the five tuber grades in calculating PIs were based on the relative market prices provided by Florida *caladium* tuber producers.

For the 2014 evaluation, beds were fumigated on 9 January with PIC-CLOR 60™ liquid fumigant (39.0% 1,3-dichloropropene and 59.6% chloropicrin) at 448 $kg \cdot ha^{-1}$. PLANTACOTE® Pluss, a controlled-release fertilizer (14N-3.9P-12.5K, 12 months, X-Calibur Plant Health Company, LLC, Summerville, S.C.), was incorporated into the bed at 336 $kg \cdot ha^{-1}$. *Caladium* seed pieces were planted on 16 and 28 April at approximately 15-cm spacing between rows and in rows. Irrigation was by seepage. *Caladium* plants were fertilized with 600 ppm of nitrogen with a commercial water-soluble fertilizer (20N-8.7P-16.6K, Southern Agricultural Insecticides, Inc., Palmetto, Fla.) on 18 September and 1 Oct. 2014. Tubers were dug from 1 December to 9 Dec. 2014, followed by the same washing, drying, weighing, grading, and counting procedures as were done in 2007.

Field plots were arranged each season in three randomized complete blocks, and each plot (1.2 $m^2$) was planted with 30 *caladium* seed pieces. Commercial cultivars [('Gingerland', 'White Wing', and 'Florida White Ruffles' (2007 only)] were included as controls in each block. Analyses of variance were conducted using the PROC GLM procedure in SAS (SAS Institute, Cary, N.C.) to compare the tuber yields of 'Cosmic Delight' to that of 'Gingerland', 'White Wing' (not patented), and 'Florida White Ruffles' (patented, U.S. Plant Pat. No. 14,402) (2007 only).

Table 1 shows the tuber weight, marketable tubers, production index, and grade distribution of the new cultivar 'Cosmic Delight' grown in Wimauma, Fla. in 2007 and 2014, as compared to those of 'Gingerland', 'White Wing', and 'Florida White Ruffles'. Values presented for each year are means of three plots in three randomized complete blocks.

TABLE 1

| | Tuber | | |
|---|---|---|---|
| Cultivars | Weight (kg) | Marketable (no.) | Production index[z] |
| | Year 2007 | | |
| Cosmic Delight | 6.1 a[y] | 48.1 a | 148.8 a |
| Gingerland | 3.7 b | 30.9 b | 91.6 b |
| White Ruffles | 1.0 c | 29.7 b | 43.3 c |
| White Wing | 0.9 c | 28.9 b | 41.4 c |
| | Year 2014 | | |
| Cosmic Delight | 4.5 a | 36.7 ns | 119.0 a |
| Gingerland | 1.3 b | 26.7 ns | 42.0 b |
| White Wing | 2.0 b | 29.7 ns | 62.3 b |

TABLE 1-continued

| Cultivars | Tuber grade distribution (%) | | | | |
|---|---|---|---|---|---|
| | Super Mammoth | Mammoth | Jumbo | No. 1 | No. 2 |
| | Year 2007 | | | | |
| Cosmic Delight | 2.7 ns | 14.5 a | 27.8 a | 37.9 ns | 17.0 b |
| Gingerland | 2.5 ns | 10.9 ab | 28.4 a | 39.8 ns | 18.4 b |
| White Ruffles | 0 ns | 1.1 bc | 4.3 b | 27.2 ns | 67.4 a |
| White Wing | 0 ns | 0 c | 4.0 b | 32.7 ns | 63.3 a |
| | Year 2014 | | | | |
| Cosmic Delight | | 14.2 a | 36.3 a | 44.9 ns | 4.5 b |
| Gingerland | | 0 b | 0 b | 60.2 ns | 39.8 a |
| White Wing | | 0 b | 16.9 | 56.8 ns | 26.3 ab |

[z]The production index is an indicator of economic value of the crop harvested and is calculated as: N (No.2s) + 2N (No. 1s) + 4N (Jumbos) + 6N (Mammoth) + 8N (Super Mammoth); where N = number of tubers in each grade. Tubers graded by maximum diameter; No. 2 (2.5 to 3.8 cm), No. 1 (3.8 to 6.4 cm), Jumbo (6.4 to 8.9 cm), Mammoth (8.9 to 11.4 cm), and Super Mammoth (>11.4 cm).
[y]Mean values with the same letters within columns are not significantly different at P ≤ 0.05.
ns: not significantly different at P ≤ 0.05.

As shown in Table 1, the tuber weight and production index of the new cultivar 'Cosmic Delight' were significantly greater than those of 'Florida White Ruffles', 'White Wing', and 'Gingerland' in both 2007 and 2014. The tuber weight of 'Cosmic Delight' was 65% to 578% greater than the tuber weight of the three controls in 2007 and 125% to 246% greater in 2014. The production index of 'Cosmic Delight' was 62% to 259% greater than that of the control cultivars in 2007 and 91% to 183% greater in 2014. Plants of 'Cosmic Delight' produced 56% to 66% more marketable tubers than the plants of the control cultivars in 2007 and 23% or 37% more marketable tubers than the control cultivars in 2014. Plants of 'Cosmic Delight' produced more Mammoth- and Jumbo-grade tubers than plants of 'White Wing' in 2007 and in 2014. Plants of 'Cosmic Delight' yielded more Mammoth- and Jumbo-grade tubers than plants of 'Gingerland' in 2014, but not in 2007. Overall, data from both 2007 and 2014 growing seasons showed that 'Cosmic Delight' had much higher tuber yields than the control cultivars 'Gingerland', 'Florida White Ruffles', and 'White Wing'.

Table 2 shows a comparison of the plant height, number of leaves, leaf length, and leaf width of the new cultivar 'Cosmic Delight' with 'Gingerland', and 'White Wing', approximately 4 months after planting 2.54-cm tuber pieces (propagules) in ground beds in full sun in 2007 and 2014. Values presented are means of data from three replications and three plants measured per plot per year and averaged over these two years.

TABLE 2

| Cultivars | Plant height (cm) | Leaves (no.) | Leaf length[z] (cm) | Leaf width[y] (cm) |
|---|---|---|---|---|
| Cosmic Delight | 34.2 a[x] | 22.8 a | 22.5 a | 13.0 a |
| Gingerland | 20.5 b | 11.0 b | 18.9 b | 11.7 ab |
| White Wing | 23.6 b | 11.7 b | 17.6 b | 9.9 b |

[z]Leaf length was measured on the largest leaves along the longest line from the leaf lobe to the leaf tip.
[y]Leaf width was measured on the largest leaves across the widest middle part.
[x]Mean values with the same letters within columns are not significantly different at P ≤ 0.05.

As shown in Table 2, plants of 'Cosmic Delight' grown in the ground beds had an average height of 34.2 cm, which were 10.6 and 13.7 cm taller than those of 'Gingerland' and 'White Wing', respectively. Plants of 'Cosmic Delight' had an average of 22.8 leaves per plant, which was 95% and 107% more than the number of leaves of 'Gingerland' and 'White Wing', respectively. Leaves of 'Cosmic Delight' were 22.5 cm long and 13.0 wide, significantly longer than the leaves of 'Gingerland' (18.9 cm) and 'White Wing' (17.6 cm), and also significantly wider than leaves of 'White Wing' (9.9 cm).

Landscape performance of 'Cosmic Delight' was evaluated on the same plots used for evaluating tuber production. A scale of 1 to 5 was used with 1 being very poor (few leaves and lack of vigor), and 5 being excellent (full plants, numerous leaves, and bright color display). Leaf sun tolerance was evaluated on a scale of 1 to 5, with 1 being very susceptible to sunburn (leaves having numerous sun-damaged areas or holes) and 5 being resistant to sunburn (no visible sun-damaged areas). Three to four evaluations were conducted in each growing season for plant performance and sunburn tolerance. Evaluations were done in July, August, and September 2007, and July, August, September, and October 2014.

Table 3 shows the landscape performance of the new cultivar 'Cosmic Delight' with 'Gingerland, 'Florida White Ruffles', and 'White Wing' when planted in ground beds in full sun in 2007 and 2014. Values presented are means of three replications in each year.

TABLE 3

| Cultivars | 2007 | | | 2014 | | | |
|---|---|---|---|---|---|---|---|
| | July | August | September | July | August | September | October |
| Cosmic Delight | 4.0 a | 4.2 a | 4.9 a | 4.0 ns | 4.1 a | 4.3 a | 5.0 a |
| Gingerland | 1.8 b | 1.7 b | 2.8 b | 3.2 ns | 2.9 b | 2.7 b | 2.3 c |
| White Ruffles | 2.2 b | 1.8 b | 2.2 c | — | — | — | — |
| White Wing | 2.6 b | 2.2 b | 2.0 c | 3.2 ns | 3.4 b | 3.3 ab | 3.2 b |

Plants were rated on a scale of 1 to 5, with 1 being very poor, 3 fair and acceptable, and 5 being excellent in plant vigor, fullness, and color display, in July, August, and September 2007, and in July, August, September, and October 2014. Mean values with the same letters within columns are not significantly different at P ≤ 0.05.
ns: Not significantly different at P ≤ 0.05.

As shown in Table 3, plants of the new cultivar 'Cosmic Delight' performed well in both 2007 and 2014 growing seasons, with performance ratings between 4.0 and 5.0. Its performance ratings were significantly higher than those of 'Gingerland' (1.7 to 2.8), 'Florida White Ruffles' (1.8 to 2.2), and 'White Wing' (2.0 to 2.6) in all three evaluations in 2007, and also significantly higher than those of 'Gingerland' (2.3 to 3.2) and 'White Wing' (3.2 to 3.4) in two or three out of four evaluations in 2014.

Table 4 shows the leaf sunburn tolerance of 'Cosmic Delight' with 'Gingerland', 'Florida White Ruffles', and 'White Wing' when tuber pieces were planted in ground beds and plants were grown in full sun in 2007 and 2014. Values presented are means of three replications in each year.

Leaf sunburn tolerance was evaluated on a scale of 1 to 5, with 1 being very susceptible to sunburn (leaves having numerous sun-damaged areas or holes) and 5 being resistant to sunburn (no visible sun-damaged areas). A total of nine evaluations were conducted over three growing seasons in July, August, and September 2007, and July, August, September, and October 2014.

TABLE 4

| | 2007 | | | 2014 | | | |
|---|---|---|---|---|---|---|---|
| Cultivars | July | August | September | July | August | September | October |
| Cosmic Delight | 3.9 a | 4.8 a | 4.7 a | 4.5 ns | 4.0 ns | 3.8 ab | 3.7 a |
| Gingerland | 3.0 b | 4.6 b | 4.0 b | 4.4 ns | 3.7 ns | 4.0 a | 2.9 b |
| White Ruffles | 3.6 a | 4.0 c | 4.0 b | — | — | — | — |
| White Wing | 3.9 a | 4.0 c | 4.7 a | 4.3 ns | 3.8 ns | 3.4 b | 3.3 b |

Plant sunburn tolerance was rated on a scale of 1 to 5, with 1 being very poor, 3 fair and acceptable, and 5 being excellent without showing any signs of leaf burns or holes caused by sunburn on leaf surfaces, in July, August, and September 2007, and in July, August, September, and October 2014.

Mean values with the same letters within columns are not significantly different at P≤0.05. ns: Not significantly different at P≤0.05.

As shown in Table 4, plants of 'Cosmic Delight' showed good to excellent sunburn tolerance in both 2007 and 2014 growing seasons, with sunburn tolerance ratings between 3.7 and 4.8. Its sunburn tolerance ratings were significantly higher than those of 'Gingerland' (2.9 to 4.6) in four of seven evaluations, better than those of 'Florida White Ruffles' (3.6 to 4.0) in two of three evaluations, and higher than those of 'White Wing' (3.3 to 4.7) in two of seven evaluations.

The suitability of the new cultivar 'Cosmic Delight' for pot plant production was evaluated by forcing tubers in 11.4-cm containers (diameter) in spring/summer 2014. No. 1-sized tubers (>3.8 cm and <6.4 cm in diameter) were planted on 24 April in a commercial potting mix (FAFARD® 3B) amended with OSMOCOTE® controlled-release fertilizer (15N-3.9P-10K, 5-6 months) at 4.3 $kg \cdot m^{-3}$; plants were grown in a greenhouse with approximately 30% light exclusion. Temperatures in the greenhouse ranged from a low of 60.8° F. at night to 86° F. during the day. Potted plants were arranged on metal benches in the greenhouse in a randomized complete block design with six replicates. Plant height, plant width, number of leaves, and foliar characteristics were recorded on 19-20 Jun. 2014, 8 weeks after planting. Quality of the potted *caladium* plants was rated on a scale of 1 to 5, with 1=very poor, unattractive, totally unacceptable as potted plants with few leaves, and 5=very attractive, full plants with a symmetrical shape, an appropriate height, and many bright, colorful leaves.

Table 5 shows a comparison of number of days to sprout, plant height, plant width, leaf number, leaf length, leaf width, and quality rating of 'Cosmic Delight' with 'Gingerland' and 'White Wing' when intact and de-eyed tubers were forced in containers in 2014.

TABLE 5

| | Days to sprout[z] | | Plant height (cm) | | Leaves (no.) | |
|---|---|---|---|---|---|---|
| Cultivars | Intact | De-eye | Intact | De-eye | Intact | De-eye |
| Cosmic Delight | 25 b | 24 ns | 26.8 ab | 26.5 ns | 13.8 ns | 26.3 ab |
| Gingerland | 21 b | 25 ns | 30.5 a | 29.3 ns | 11.0 ns | 30.2 a |
| White Wing | 30 a | 27 ns | 24.8 b | 24.8 ns | 13.5 ns | 20.3 b |
| | Leaf length (cm) | | Leaf width (cm) | | Quality rating | |
| Cultivars | Intact | De-eye | Intact | De-eye | Intact | De-eye |
| Cosmic Delight | 23.5 a | 18.3 ns | 15.7 a | 10.9 a | 3.0 ns | 3.9 b |
| Gingerland | 21.3 b | 16.1 ns | 15.1 a | 9.6 ab | 3.0 ns | 4.4 a |
| White Wing | 21.8 ab | 17.2 ns | 11.6 b | 8.1 b | 3.3 ns | 4.0 ab |

[z]Number of days from planting to the first unfurled leaf.
Mean separation within column for each cultivar by Fisher's least-significant-difference test at P ≤ 0.05.

As shown in Table 5, intact tubers of 'Cosmic Delight' sprouted 25 days after planting, approximately 5 days earlier than those of 'White Wing'. Plants of 'Cosmic Delight' from the intact tubers were similar to plants of 'White Wing', having similar plant heights, similar numbers of leaves, similar leaf lengths, and similar plant quality ratings, except that the leaves of 'Cosmic Delight' were 4.1 cm wider leaves than those of 'White Wing'. When tubers were planted intact, 'Cosmic Delight' and 'Gingerland' also had similar sprouting time (25 and 21 days), similar plant heights, similar numbers of leaves, similar leaf widths, and similar plant quality ratings (3.0 and 3.0). The exception was that leaves of 'Cosmic Delight' were 2.2 cm longer than those of 'Gingerland'.

De-eyed tubers of 'Cosmic Delight' sprouted in 24 days after planting, similar to the de-eyed tubers of 'White Wing' (27.3 days) and 'Gingerland' (24.5 days). There were no significant differences among plants of 'Cosmic Delight', 'White Wing', and 'Gingerland' forced from de-eyed tubers in plant heights (24.6 to 29.3 cm), numbers of leaves (20.3 to 30.2), and leaf lengths (16.1 to 18.3 cm). However, plants of 'Cosmic Delight' had wider leaves than plants of 'White Wing' (10.9 vs. 8.1 cm) and received a lower plant quality rating than plants of 'Gingerland' (3.9 vs. 4.4).

'Cosmic Delight' produced marketable pot plants without tuber de-eyeing. However, this treatment resulted in pot plants with improved quality. Plants of 'Cosmic Delight' from de-eyed tubers had 91% more but smaller (22% shorter and 31% narrower) leaves, and received a higher quality rating (3.9 vs. 3.0) than plants from intact tubers.

We claim:

1. A new and distinct *Caladium* plant named 'Cosmic Delight' as illustrated and described herein.

* * * * *